United States Patent [19]

Hummert et al.

[11] Patent Number: 4,859,940
[45] Date of Patent: Aug. 22, 1989

[54] APPARATUS FOR DETECTING ONSET OF SLAG ENTRAINMENT IN A MOLTEN METAL STREAM

[75] Inventors: George T. Hummert, Oakmont; Robert M. Slepian, Pittsburgh, both of Pa.; Lawrence R. Westrick, Grosse Ile, Mich.

[73] Assignee: Westinghouse Electric Corp., Pittsburgh, Pa.

[21] Appl. No.: 94,983

[22] Filed: Sep. 9, 1987

[51] Int. Cl.$^4$ .................. G01N 27/74; G01R 33/12
[52] U.S. Cl. .................. 324/204; 324/226; 324/237; 164/154; 164/453
[58] Field of Search .................. 324/204, 225–228, 324/233–234, 236, 237, 238, 239, 260, 261, 262; 164/154, 4.1, 453, 451

[56] References Cited

U.S. PATENT DOCUMENTS

| Re. 24,420 | 1/1958 | Fielden | 324/65 |
|---|---|---|---|
| 2,645,563 | 7/1953 | Jensen | 23/230 |
| 2,919,413 | 12/1959 | Charles | 331/65 |
| 3,006,188 | 10/1961 | Handel et al. | 73/194 |
| 3,329,906 | 7/1969 | Bringert | 331/65 |
| 3,448,375 | 6/1969 | Meuniek | 324/34 |
| 3,511,580 | 5/1970 | Echkardt et al. | 417/48 |
| 3,602,806 | 8/1971 | Czekajewski | 324/40 |
| 3,609,580 | 9/1971 | Thompson | 331/65 |
| 3,715,919 | 2/1973 | Kishimoto et al. | 324/204 X |
| 3,719,882 | 3/1973 | Pincus | 324/3 |
| 3,806,690 | 4/1974 | Frungel | 219/10.77 |
| 3,833,850 | 9/1974 | Weber | 324/41 |
| 3,942,105 | 3/1976 | Bondarenko et al. | 324/243 X |
| 4,140,300 | 2/1979 | Gruner et al. | 266/45 |
| 4,160,204 | 7/1979 | Holmgren et al. | 324/207 |
| 4,173,299 | 11/1979 | Kollberg et al. | 222/594 |
| 4,187,462 | 2/1980 | Haker et al. | 324/204 |
| 4,195,260 | 3/1980 | Sakamoto et al. | 324/204 |
| 4,222,506 | 9/1980 | Sakashita et al. | 222/600 |
| 4,279,149 | 7/1981 | Block | 73/290 R |
| 4,373,705 | 2/1983 | Yamada | 266/227 |
| 4,446,427 | 5/1984 | Lovrenich | 324/207 |
| 4,451,787 | 5/1984 | Bergstrand | 324/242 |
| 4,460,031 | 7/1984 | Wiesinger et al. | 164/150 |
| 4,462,574 | 7/1984 | Keeman et al. | 266/45 |
| 4,475,083 | 10/1984 | Linder | 324/233 X |
| 4,523,146 | 6/1985 | Champaigne | 324/204 |
| 4,529,029 | 7/1985 | Block | 164/453 |
| 4,590,424 | 5/1986 | Girot et al. | 324/204 |
| 4,611,127 | 9/1986 | Ibrahim et al. | 307/116 |
| 4,635,832 | 1/1987 | Angerek et al. | 222/590 |
| 4,682,645 | 7/1987 | Kinolmann | 164/453 |

FOREIGN PATENT DOCUMENTS

| 52-29800 | 5/1977 | Japan . |
| 55-97846 | 7/1980 | Japan . |
| 57-56154 | 4/1982 | Japan . |
| 59-13961 | 1/1984 | Japan . |
| 0609595 | 3/1979 | Switzerland . |

OTHER PUBLICATIONS

IBM Technical Disclosure Bulletin vol. 14, No. 4, Sep. 1971, p. 1220.

Primary Examiner—Reinhard J. Eisenzopf
Assistant Examiner—Warren S. Edmonds

[57] ABSTRACT

A slag detector apparatus for detecting onset of 5% or less slag entrainment in a stream of molten metal employs a detection coil having an axial length at least equal to the length of a globule of molten metal in the stream being composed of a continuous succession of recurring cyclical globules of molten metal, and an impedance detector for periodic sampling and smoothing of the fluctuations of the terminal impedance of the detector coil corresponding to the fluctuating cross-sectional dimension of the stream. The detector coil is part of a signal sensitivity enhancement circuit in the apparatus which also includes a tunable capacitor connected with the detector coil. The capacitor is used for tuning the circuit to its resonance frequency so that the capacitive reactance of the circuit due to the presence of the capacitor cancels the inductive reactance of the circuit due to the presence of the coil so as to leave only an impedance that is due to resistance of the coil.

6 Claims, 3 Drawing Sheets

APPARATUS FOR DETECTING ONSET OF SLAG ENTRAINMENT IN A MOLTEN METAL STREAM

CROSS REFERENCE TO RELATED APPLICATIONS

Reference is hereby made to the following copending applications dealing with related subject matter and assigned to the assignee of the present invention:

1. "Electromagnetic Apparatus For Restraining The Flow Of Molten Metal From A Vessel" by Christropher C. Alexion et al, assigned U.S. Ser. No. 698,485 and filed Feb. 5, 1985.

2. "Improved Discrete Excitation Coil Producing Seal At Continuous Casting Machine Pouring Tube Outlet Nozzle/Mold Inlet Interface" by Dennis Pavilik et al, assigned U.S. Ser. No. 050,272 and filed May 15, 1987.

3. "Liquid Metal Electromagnetic Flow Control Device Incorporating A Pumping Action" by Robert M. Del Vecchio et al, assigned U.S. Ser. No. 070,017 and filed July 6, 1987.

BACKGROUND OF THE INVENTION

1. Field of the Invention

The present invention relates generally to a process of continuous casting of steel and, more particularly, is concerned with apparatus for detecting the onset of slag entrainment in a stream of molten steel such as occurs in the continuous casting process as a ladle empties into a tundish.

2. Description of the Prior Art

Continuous casting of steel billets, blooms and slabs is a process that converts batches of molten steel prepared in furnaces into a continuous product. This process consists of several intervening steps in which the steel receives the final chemical treatment and is held ready for pouring into the casting mold. In the first step, the steel is poured from the furnace into a transfer ladle and subjected to compositional analysis and modification, while maintained at the appropriate superheat temperature required for casting. In the next step, the ladle is moved into position over a tundish and molten steel is transferred in a continuous stream via gravity feed through a slide gate valve in the bottom of the ladle to the tundish. The tundish, which holds a smaller volume of steel, is stationarily positioned spaced above the mold and includes nozzles for guiding steel into molds.

As the ladle empties, its discharge into the tundish is terminated, and another ladle is brought into position to keep the tundish replenished with molten steel. Each ladle of molten steel is referred to as a "heat", and many heats are required for one continuous casting run. In order to maintain high quality and a uniform cast product, it is important to maintain a uniform quality of molten steel in the succession of heats.

Slag in the molten steel can reduce the uniform quality of the product if the slag is allowed to flow into the tundish from the ladle. Slag, which consists of various oxides created in the furnace and ladle, has a lower density than steel and consequently floats on the surface of the molten steel. Parenthetically, its presence does serve a useful purpose in that it forms a floating insulative layer which helps to maintain the superheat temperature of the molten steel.

Since the molten steel is withdrawn through the gate valve at the bottom of the ladle, slag is kept from contaminating the tundish (and the finished product) since it floats on the top surface. This technique works until near the end of each heat, when slag tends to mix with steel due to vortexing effects created by the steel discharge. In order to minimize contamination, the level of steel in the ladle is monitored visually and the flow is terminated when it appears to be near the onset of vortexing (i.e. slag entrainment) in the discharge stream. Usually, but not always, the flow is terminated early, and valuable steel is subsequently scraped along with slag for recycling in the furnace. Ocassionally, flow is not terminated in time, and large volumes of slag are sucked into the discharge and into the tundish. Using the visual sighting method mentioned above, the process is strictly a matter of judgement based upon experience. The tendency is to maintain the quality of the finished product by cutting flow of uncontaminated steel. For a typical caster, the net worth of scraped steel from each heat can be several hundred-thousand to several million dollars annually.

Several devices for slag detection appear in the prior art. Representative of such prior art devices are the ones disclosed in Japanese Pat. Nos. 52-29800 and 57-56154 and the Slag Detector available from Voest-Alpine. In particular, the Japanese patents both disclose devices for detecting slag outflow from a vessel containing molten metal. The devices use a coil to detect the difference in conductivity between the molten metal and the slag. Japanese Pat. No. 52-29800 allows eddy currents to be generated within the flow of molten metal. The effluence of slag in the flow is reflected in a change in the coil's impedance which is converted to a voltage in a bridge circuit. In Japanese Pat. No. 57-56154, the impedance change due to slag is measured by an impedance measuring device and then run through a bandpass filter. The Voest-Alpine device uses a diffrrential coil mounted on the ladle shroud. The coil generates eddy currents in the casting stream. The difference in electrical conductivity is used to distinguish slag and liquid steel. The induction changes in the coil are sensed by a bridge, amplified by means of a carrier frequency amplifier, and then rectified.

While these prior art devices might operate satisfactorily under the limited range of conditions for which they were designed, another critical condition that typically is present in molten steel discharge appears not to have been addressed by these prior art devices. This condition is fluctuations in the flow velocity of the molten steel discharge that could cause false alarms by indicating the onset of slag entrainment when, in fact, no slag is present. Consequently, a need still exists for a suitable apparatus for detecting the onset of slag entrainment in the steel discharge from a ladle in a continuous caster.

SUMMARY OF THE INVENTION

The present invention provides a slag detector apparatus designed to satisfy the aforementioned needs. The slag detector apparatus of the present invention is operable for detecting the onset of slag entrainment in a stream of molten steel having an undulating cross-sectional dimension due to its fluctuating flow velocity, such as normally occurs in a continuous casting process as the ladle empties its heat of molten steel into a tundish. The slag detector apparatus includes a single phase AC detector coil and an impedance detector. The detector coil is located adjacent to a ladle shroud and electromagnetically coupled to the molten stream such that changes in electrical conductivity (i.e. resistance) due to slag entrainment show up as a corresponding change in the terminal impedance of the detector coil.

The detector coil preferably has an axial length at least equal to the length of one of a continuous succession of recurring cyclical globules of molten steel which form the stream thereof. With such relationship of the coil length relative to globule length, no change in electrical conductivity of the coil will be detected that is due merely to the variation in cross-sectional dimension of the stream from the upstream to downstream end of a single globule thereof. This form of construction is, effectively, a means for improving the signal to noise ratio of the slag detector apparatus in that undesirable signal fluctuations or noise generated by flow undulations are minimized at the coil's terminals.

The slag detector apparatus also includes a circuit to improve the signal sensitivity of the apparatus. The circuit incorporates the detector coil and a tunable capacitor connected with the coil for tuning the circuit to its resonance frequency so that capacitive reactance of the circuit cancels its inductive reactance leaving only an impedance that is resistive. Since molten steel is a conductor, the equivalent parallel resistance in the coil circuit is low at 0% slag flow. On the other hand, since slag is an insulator, the parallel equivalent resistance of the circuit is hgh at 100% slag flow. However, the purpose of the slag detector apparatus is to be capable of detecting a condition of 5% or less slag entrainment in the molten steel stream so that actions can then be taken to shut off further discharge from the ladle to the tundish.

In order to achieve reliable, repeatable detection sensitivity in the 5% or less range of slag entrainment, particular attention is given in the present invention to the problem of eliminating noise generated by fluctuations in the flow velocity of the molten steel. Two ways this problem is addressed have already been mentioned, that being, by (1) selecting the axial length of the detector coil to be at least equal to one cyclical globule of steel and, (2) by selecting the optimum excitation frequency. Yet another way this problem is addressed is by utilizing suitable apparatus such as a commercially-available computer, to sample and smooth (i.e. time average) impedance fluctuations taking into account the time of the signal detection relative to the stage in the discharge of the molten steel (i.e. heat time) from the ladle. On-line or real-time computer analysis of signal variations versus heat time may be carried out to ensure reliable slag onset detection.

These and other advantages and attainments of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which.

DETAILED DESCRIPTION OF THE INVENTION

Figure 1:
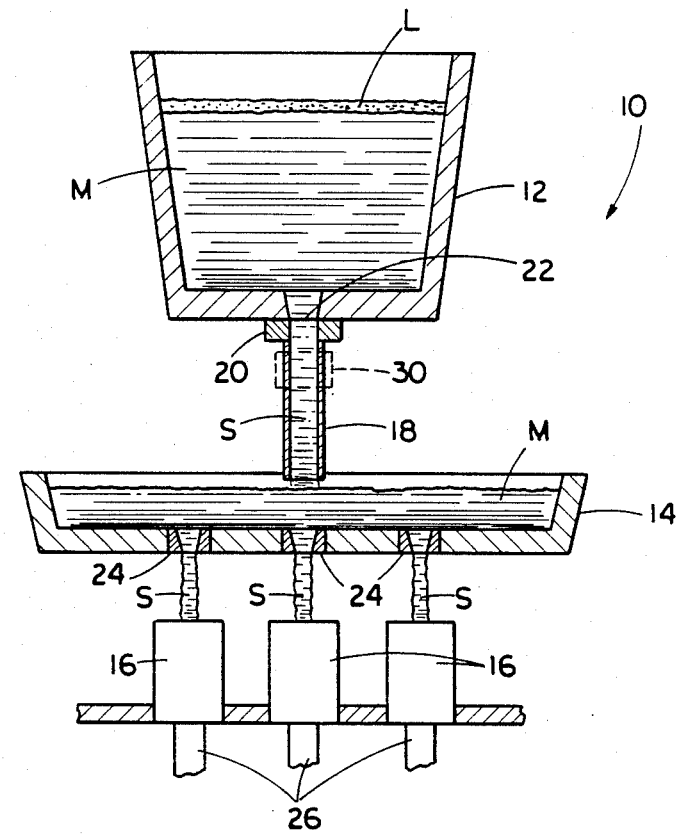
FIG. 1 is a schematic diagram of a conventional continuous casting line wherein the slag detector apparatus of the present invention can be employed.

In the following description, like reference characters designate like or corresponding parts throughout the several views. Also in the following description, it is to be understood that such terms as "forward", "rearward", "left", "right", "upwardly", "downwardly", and the like, are words of convenience and are not to be construed as limiting terms.

Referring now to the drawings, and particularly to FIG. 1, there is shown a schematic representation of a conventional vertical continuous casting line, generally designated by the numeral 10. The continuous casting line 10 includes a ladle 12, a tundish 14, and a plurality of casting molds 16 disposed below the tundish. Hot molten metal M, such as steel, issues in a stream from the ladle 12 through a pouring tube or shroud 18 into the tundish 14. The discharge of molten metal M from the ladle 12 is controlled by operation of a slide gate valve 20 positioned immediately below a bottom orifice 22 in the ladle 12 and above the shroud 18. The tundish 14, in turn, infeeds the molten metal M contained therein through a series of spaced nozzles 24 formed in its bottom and in a corresponding number of free streams S to upper inlet ends of the casting molds 16. Continuous solid strands 26 of metal are formed around a liquid core in the respective casting molds 16 and withdrawn from the lower outlet ends thereof. The continuous or strands 26 are then fed through a spray zone (not shown) where they are progressively cooled to solidify the liquid cores and thereafter the strands are fed between rolls of a straightner (not shown).

As explained earlier, a layer of slag L, having a density less than that of the molten metal, is always present floating on the surface of the pool of molten metal M contained in the ladle 12. The slag L forms an insulative layer which helps to maintain the superheat temperature of the molten metal M in the ladle 12; however, it can reduce the uniform quality of the product if it is allowed to flow into the tundish 14 (and therefrom into the molds 16) from the ladle 12. Heretofore, in order to minimize contamination, the level of molten metal M in the ladle 12 was monitored visually and the flow thereof terminated usually prematurely in order to avoid the onset of slag entrainment in the discharge stream. As a result, a significant amount of uncontaminated steel was scraped along with the slag for recycling through the furnace (not shown) in order to prevent contamination of the finished product.

Figure 2:
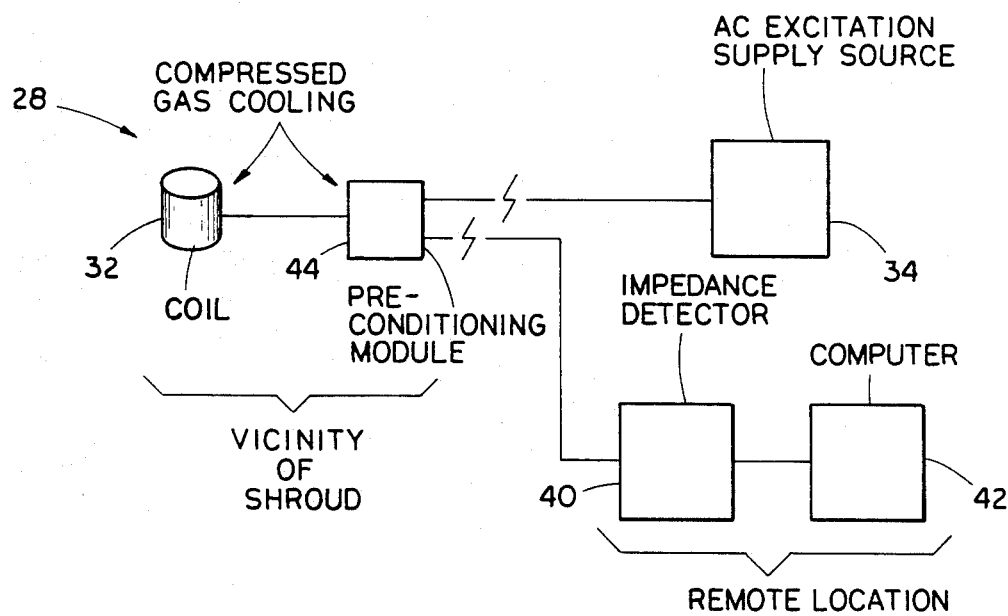
FIG. 2 is a schematic block diagram of the slag detector apparatus of the present invention.
Figure 3:
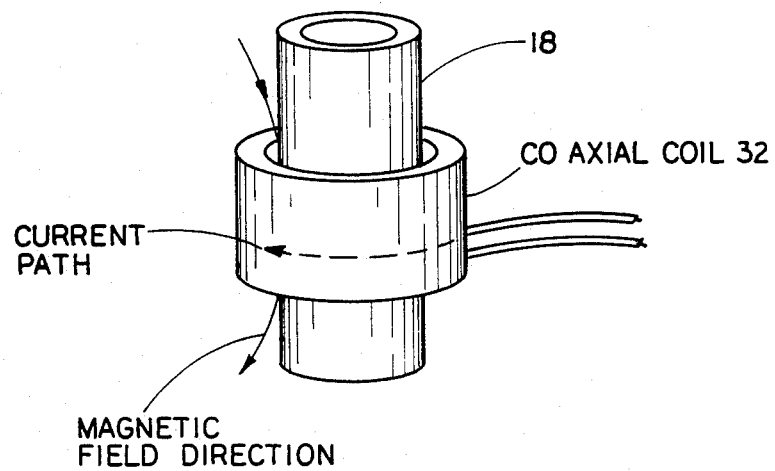
FIG. 3 is an enlarged perspective view, showing in fragmentary form a molten steel discharge shroud which extends between the ladle and tundish of the continuous casting line and showing a detector coil coaxially-arranged about the shroud and within a cooling device.

Referring to FIG. 2, there is shown the slag detector apparatus 28 of the present invention which is employed to reduce the amount of uncontaminated molten metal M which is scraped with the slag L at the termination of discharge of each heat of molten material from a ladle 12. It is estimated that large savings can be realized if the metal lost on each heat because of slag entrainment can be reduced by accurately measuring slag content of the molten metal discharging from the ladle 12. The components of the apparatus 28 are represented in block form in FIG. 2 since they are individually well-known in the art, and to reproduce them in detail would only serve to increase the complexity of the explanation of the apparatus 28 without adding to its clarity.

Figure 4:
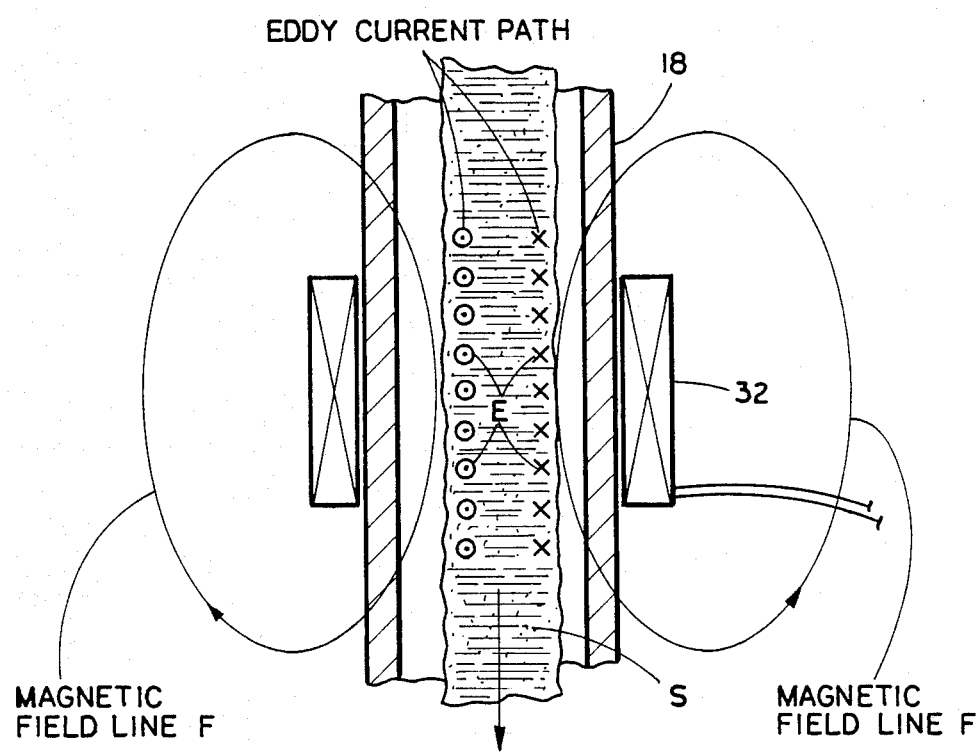
FIG. 4 is a schematic cross-sectional view of the shroud, molten stream and slag detector coil.
Figure 5:
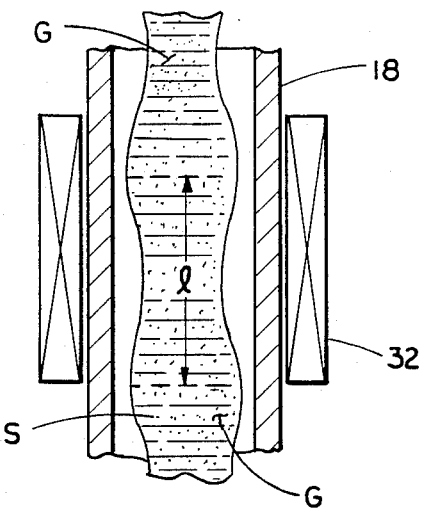
FIG. 5 is a schematic representation of the succession of globules of molten steel which make up the discharge stream and of the detector coil having an axial length at least equal to the length on a single globule.

Prior detection devices apparently operated on the assumption that the stream of molten metal issuing from the ladle 12 had a constant flow velocity and thus was cylindrical in shape with a constant cross-sectional dimension, as seen in FIG. 4. Unlike detection devices proposed hereto, the slag detector apparatus 28 of the present invention is operable for detecting the onset of slag entrainment in a stream of molten metal M having a fluctuating flow velocity producing a variable or undulating cross-sectional dimension as depicted in FIG. 5. Underlying the present invention, is the realization that a molten metal stream having a fluctuating, as opposed to a constant, flow velocity is what normally occurs in a continuous casting process as the ladle 12 empties its heat of molten metal into the tundish 14.

As known in the prior art, the detection scheme used herein is also based upon the difference in conductivity of molten metal (a conductor) and slag (an insulator). As seen in FIGS. 2-5, the slag detector apparatus 28 employs an annular-shaped electrical single phase AC detector coil 32 mounted co-axially about the shroud 18 and with the discharge stream flowing therein in the region of the dashed box 30 in FIG. 1. Excited by an alternating current supply source 34, the magnetic field F of the detector coil 32 generates eddy currents E in the molten metal stream M passing through the shroud 18 and the coil 32. Eddy current losses in the molten metal (ohmic power losses) are reflected to the coil 32 in terms of an effective change in impedance at the coil's terminals. Thus, the detector coil 32 by being located adjacent to the ladle shroud 18 is electromagnetically coupled to the molten stream S such that changes in electrical conductivity (i.e. resistance) due to slag entrainment shows up as a corresponding change in the terminal impedance of the detector coil. In effect, the coil/molten metal configuration is a specialized transformer, where the coil acts as the primary winding and the molten metal core the secondary winding. Changes in bulk conductivity of the metal due to entrained slag will be reflected as changes in terminal impedance.

However, in the case of the molten metal stream configuration seen in FIG. 5, changes in bulk conductivity of the metal detected by the coil is also due to variation in the mass of the metal in the stream S thereof passing through the coil 32. The variation in cross-sectional dimension of the stream S appears to be repetitive in nature such that the outer surface of the stream has an undulating configuration. In effect, the stream S appears to be composed of a continuous succession of recurring cyclical globules G of flowing molten metal.

To cancel out or compensate for the effect of this fluctuating configuration of the stream S on the conductivity of the detector coil 32, the coil preferably has an axial length at least equal to the length l of one cycle of the globules G of molten metal which form the stream thereof, for instance six to ten inches. With such relationship of the coil length relative to globule cycle length, no change in electrical conductivity of the coil 32 will be detected that is due merely to the variation in cross-sectional dimension of the stream from the upstream to downstream end of the single globule cycle.

The signal to noise ratio of the slag detector apparatus is also improved over the prior art by exciting the coil at the optimum frequency such that the skin depth or depth of magnetic field pentration is approximately equal to the radius of the flow stream. Both computer modeling and laboratory tests with solid steel rods indicate that signal sensivity to excitation frequency is not extremely critical in that deviations from the optimum of $+/-20\%$ affect the signal by less than 10%. Deviations greater than 50%, though, will reduce the signal by 50% or more depending upon the magnitude of deviation. Thus it is important to maximize the signal level by selecting the operating frequency (or skin depth) to correspond to the average size of the flow stream.

Figure 6:
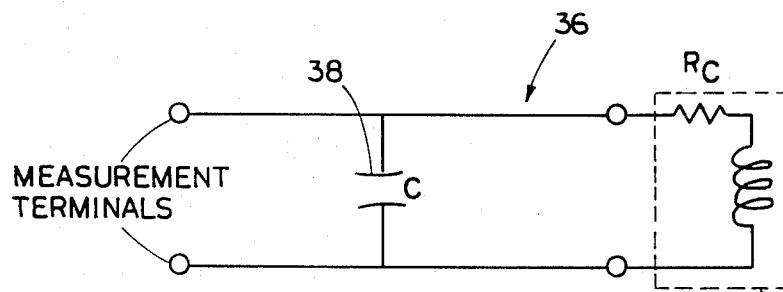
FIG. 6 is a schematic diagram of a resonant circuit employed by the slag detector apparatus.

The slag detector apparatus 28 also includes a circuit 36 to improve the signal sensitivity of the apparatus. The circuit 36 incorporates the detector coil 32 and a tunable capacitor 38 connected in parallel (although alternatively a series arrangement could be used) with the coil 32, as shown in FIG. 6, for tuning the circuit 36 to its resonance frequency so that capacitive reactance of the circuit cancels its inductive reactance leaving only an impedance that is resistive. It is the value of the latter impedance that is desired to be detected and measured. Since molten steel is a conductor, parallel resistance of the circuit at 0% slag flow would be low. On the other hand, since slag is an insulator, parallel resistance of the circuit at 100% slag flow would be high. However, the purpose of the slag detector apparatus 28 is to be capable of detecting a condition of 5% or less slag entrainment in the molten steel stream S so that actions can then be taken, either automatically or manually, to operate the gate valve 20 so as to shut off further discharge of molten metal M from the ladle 12 to the tundish 14.

In order to achieve reliable, repeatable detection sensitivity in the 5% or less range of slag entrainment, particular attention is given in the present invention to the problem of eliminating noise generated by fluctuations in the flow velocity of the molten metal stream S. One way this problem is addressed has already been mentioned, that being, by selecting the axial length of the detector coil 32 to be at least equal to the spatial variation of typical flow perturbations, or as described previously herein, the length l of one cyclical globule G of molten metal. The other way this problem is addressed is by utilizing a suitable detecting and computing means, such as a commercially-available impedance detector 40, such as a Hewlett-Packard 4274A, and a conventional computer 42. The impedance detector 40 is connected to the resonant circuit 36. The resonant tunable capacitor 3 and conditioning amplifiers (not shown) are housed in a pre-conditioning module 44 located near the detector coil 32. The module 44 is included as a means for locating the resonant circuit components (coil 32 and capacitor 38) in close proximity, thereby minimizing effects of stray capacitance and cable resistance. Since the module 44 is located in a region beneath the ladle 12 where it is subject to ambient temperatures approaching 500 degrees F., the module 44 is cooled by compressed gas to protect the electronic components. The detector coil 32 is surrounded by a device (not shown) for cooling the coil by the compressed gas also. As indicated in FIG. 2, the impedance detector 40, AC power supply source 34 and computer 42 are located remote from the severe environment of the shroud/ladle region.

The impedance detector 40 and computer 42 cooperate to sample and smooth (i.e. time average) impedance fluctuations due to stream mass fluctuations taking into account the time of the signal detection relative to the stage in the discharge of the molten steel (i.e. heat time) from the ladle 12. For instance, slag is not expected near the beginning of a heat discharge where the flow is expected to be 100% steel at full flow capacity. Then, as the tundish 14 fills, flow is reduced (via regulation of the slide gate valve 20 beneath the ladle 12) to, say, 50% of maximum, yet containing 0% slag. This condition prevails for most of the pouring interval, until near the end when slag entrainment begins. On-line or real-time computer analysis of signal variations versus heat time may be carried out to ensure reliable slag onset detection.

Figure 7:
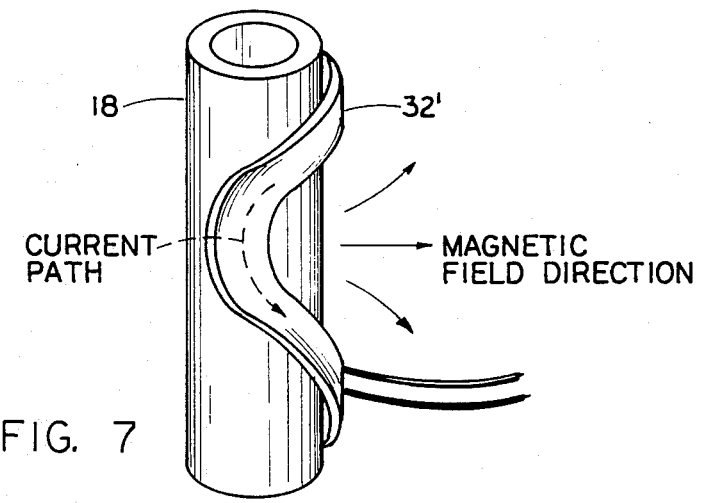
FIG. 7 is an alternative form of the detector coil which can be used in the slag detector apparatus.

Although an annular concentric coil configuration is described above, note that in FIG. 7 another possible embodiment of the coil is illustrated, being designated 32'. Coil 32' has a saddle shaped configuration and is mounted along a side of the shroud 18. This configuration has the advantage of being readily removed from the shroud region for repair or calibration without disturbing the continuous process. The concentric configuration previously described may be removed only between heats when the shroud is detached from the ladle and swung away from the immediate tundish area.

A computer model of a conceptual coil winding was used to analyze impedance changes. Tabulated in Table 1, these results indicate that detection of 5% or less slag entrainment is feasible.

TABLE I
Calculated Impedance Variations

| | Slag Content | |
|---|---|---|
| | 100% | 0% |
| Coil Resistance | 0.600 | 1.355 |
| Coil Inductance | 6.18 mH | 6.02 mH |
| Parallel Resistance | 629.0 | 264.0 |
| Parallel Impedance | 629.0 | 246.0 |
| | <0° | <20° | coil: 200 turns
parallel capacitance = 16 μf
resonant frequency with 6.18 mH at 500 Hz Referring to the last line of the table, it can be seen that changing the stream core material from 100% slag to 100% steel produces an impedance change of approximately 629Ω<0° to 246Ω<20°. To a first approximation, proportional changes in slag content will produce proportional impedance variation, and, therefore, changes in the order of 19Ω and 1° for a 5% variation in slag content. This is well within the sensitivity range of impedance detectors. For these data the following parameters were used:

Shroud ID=4.5 in
Shroud OD=6.5 in
Coil length (axial)=6.0 in
Coil thickness (radial)=1.0 in
Frequency=500 Hz
Turns=200

These parameters were not optimized and were chosen for illustrative purposes only. Computer modeling also indicates that it is desirable to choose an optimum excitation frequency such that the skin depth of the induced eddy currents in the core is approximately equal to the radius of the core, where skin depth is given by $(PI*F*MU*SIGMA)^{-\frac{1}{2}}$ and F, MU, SIGMA are the frequency, permeability, and conductivity, respectively.

Referring to the first two lines of the Table, it can be seen that inductance changes are rather minimal compared to series resistance changes —inductance changes by approximately 3% while resistance changes by a factor of two. Proportional changes for 5% slag content yield a series resistance change of 0.037 ohms and a negligible change in inductance. An alternative detection scheme, therefore, is to use a commercial impedance meter connected directly to the coil with no resonant capacitor, and to record variations of series resistance.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

We claim:

1. A slag detector apparatus for detecting the onset of slag entrainment in a stream of molten metal having a fluctuating cross-sectional dimension and being composed of a continuous succession of recurring cyclical globules of molten metal, each globule cycle being of approximately length "l", said apparatus comprising:
    (a) an AC detector coil located adjacent the stream;
    (b) means for applying an a.c. excitation to said detector coil for electromagnetically coupling said detector coil to the stream of molten metal such that changes in electrical conductivity of the molten metal in the stream thereof due to slag entrainment are reflected as a corresponding change in terminal impedance of said detector coil; and
    (c) means for detecting the change in terminal impedance of said detector coil;
    (d) said detector coil having an axial length at least equal to the length "l" of one cycle of the globules composing the stream of molten metal for nullifying any change in terminal impedance of said detector coil due to the presence of the fluctuating cross-sectional dimension of the molten metal stream.

2. The slag detector apparatus as recited in claim 1, further comprising a signal sensitivity enhancement circuit which includes:
    said detector coil; and
    a tunable capacitor connected with said detector coil for tuning said circuit to its resonance frequency so that the capacitive reactance of said circuit due to the presence of said capacitor cancels the inductive reactance of said circuit due to the presence of said coil so as to leave only an impedance that is due to the resistance of said coil.

3. The slag detector apparatus as recited in claim 2, wherein said tunable capacitor is connected in parallel with said detector coil.

4. The slag detector apparatus as recited in claim 2, wherein said terminal impedance detecting means includes an impedance detector connected to said circuit for periodic sampling and smoothing of the fluctuations of the terminal impedance of said detector coil.

5. The slag detector apparatus as recited in claim 1, wherein said terminal impedance detecting means includes an impedance detector connected to said coil.

6. A slag detector apparatus for detecting the onset of slag entrainment in a stream of molten metal having a fluctuating cross-sectional dimension and being composed of a continuous succession of recurring cylcical globules of molten metal, each globule cycle being of approximate length "l", said apparatus comprising:

(a) an AC detector coil located adjacent the stream;
(b) means for applying an a.c. excitation to said detector coil for electromagnetically coupling said detector coil to the stream of molten metal such that changes in electrical conductitivity of the molten metal in the stream thereof due to slag entrainment are reflected as a corresponding change in terminal impedance of said detector coil; and
(c) means for detecting the change in terminal impedance of said detector coil, said terminal impedance detecting means including an impedance detector connected to said coil for periodic sampling and smoothing of the fluctuations of the terminal impedance of said detector coil;
(d) said detector coil having an axial length at least equal to the length "l" of one cycle of the globules composing the stream of molten metal for nullifying any change in terminal impedance of said detector coil due to the presence of the fluctuating cross-sectional dimension of the molten metal stream.

* * * * *